United States Patent [19]

Sarr

[11] Patent Number: 4,799,168

[45] Date of Patent: Jan. 17, 1989

[54] DATA RECORDING APPARATUS FOR AN ULTRASONIC INSPECTION SYSTEM

[75] Inventor: Dennis P. Sarr, Kent, Wash.

[73] Assignee: The Boeing Company, Del.

[21] Appl. No.: 815,050

[22] Filed: Dec. 31, 1985

[51] Int. Cl.$^4$ ............................................. G01N 29/04
[52] U.S. Cl. .................... 364/507; 364/552; 73/625; 73/611; 73/614; 346/33 F; 346/33 EC
[58] Field of Search ....................... 364/507, 552, 550; 73/600, 602, 604, 609, 618, 614, 622, 611, 623, 624, 625, 628, 637, 638, 640; 346/33 P, 33 F, 33 EC

[56] References Cited

U.S. PATENT DOCUMENTS

| | | | |
|---|---|---|---|
| 3,051,956 | 8/1962 | Theobald | 346/141 |
| 3,363,226 | 1/1968 | Murphree | 340/3 |
| 3,570,279 | 3/1971 | Davies | 73/67.9 |
| 3,624,370 | 11/1971 | Gray, Jr. | 235/151.3 |
| 3,633,211 | 1/1972 | Batzdorff | 346/14 |
| 3,815,144 | 6/1974 | Aiken | 346/35 |
| 3,885,224 | 5/1975 | Klahr | 340/5 MP |
| 3,942,149 | 3/1976 | Westfall, Jr. | 340/3 R |
| 3,961,523 | 6/1976 | Cornforth | 73/622 |
| 3,981,184 | 9/1976 | Matay | 364/552 |
| 3,986,011 | 10/1976 | Poole et al. | 235/151.22 |
| 3,986,389 | 10/1976 | Mesina et al. | 73/611 |
| 4,038,664 | 7/1977 | Muir | 346/1 |
| 4,050,057 | 9/1977 | Backman, Jr. | 340/3 F |
| 4,055,989 | 11/1977 | Henry, Jr. et al. | 73/622 |
| 4,088,028 | 5/1978 | Hildebrandt | 364/507 |
| 4,096,484 | 6/1978 | Ferre et al. | 346/33 EC |
| 4,147,065 | 4/1979 | Lather et al. | 73/611 |
| 4,160,385 | 7/1979 | Gromlich et al. | 73/622 |
| 4,160,386 | 7/1979 | Jackson et al. | 73/622 |
| 4,167,121 | 9/1979 | Mauch | 73/640 |
| 4,205,395 | 5/1980 | Shortridge | 367/115 |
| 4,207,620 | 6/1980 | Morgera | 367/88 |
| 4,224,672 | 9/1980 | Leleu et al. | 346/33 R |
| 4,226,122 | 10/1980 | Lund et al. | 73/609 |
| 4,290,308 | 9/1981 | Dau | 73/602 |
| 4,524,622 | 6/1985 | Suzaki et al. | 73/640 |
| 4,660,419 | 4/1987 | Derkacs et al. | 73/622 |

Primary Examiner—Parshotam S. Lall
Assistant Examiner—V. N. Trans
Attorney, Agent, or Firm—Finnegan, Henderson, Farabow, Garrett & Dunner

[57] ABSTRACT

A multi-channel ultrasonic inspection system includes an ultrasonic inspection unit which generates ultrasonic inspection pulses, supplies the pulses to a part being inspected, produces an output signal proportional to the level of echo pulses received within a predetermined gate time window following generation of the inspection pulses, and generates an alarm signal whenever the output signal exceeds a predetermined gate level. The system also includes data recording apparatus having a microcomputer, a mathematics processor chip, a control panel, and a printer. A gate reference level for each channel is stored by the microcomputer by pressing a channel button on the control panel, supplying inspection pulses to a workpiece having a standard defect, and adjusting the gain or gate level of the ultrasonic inspection unit until an alarm signal is generated. The operator then presses a START button which causes the reference levels to be printed. When an echo pulse is received which exceeds the gate reference level, an alarm signal is generated which causes a print-out of the difference between the defect echo pulse level and the gate reference level.

11 Claims, 5 Drawing Sheets

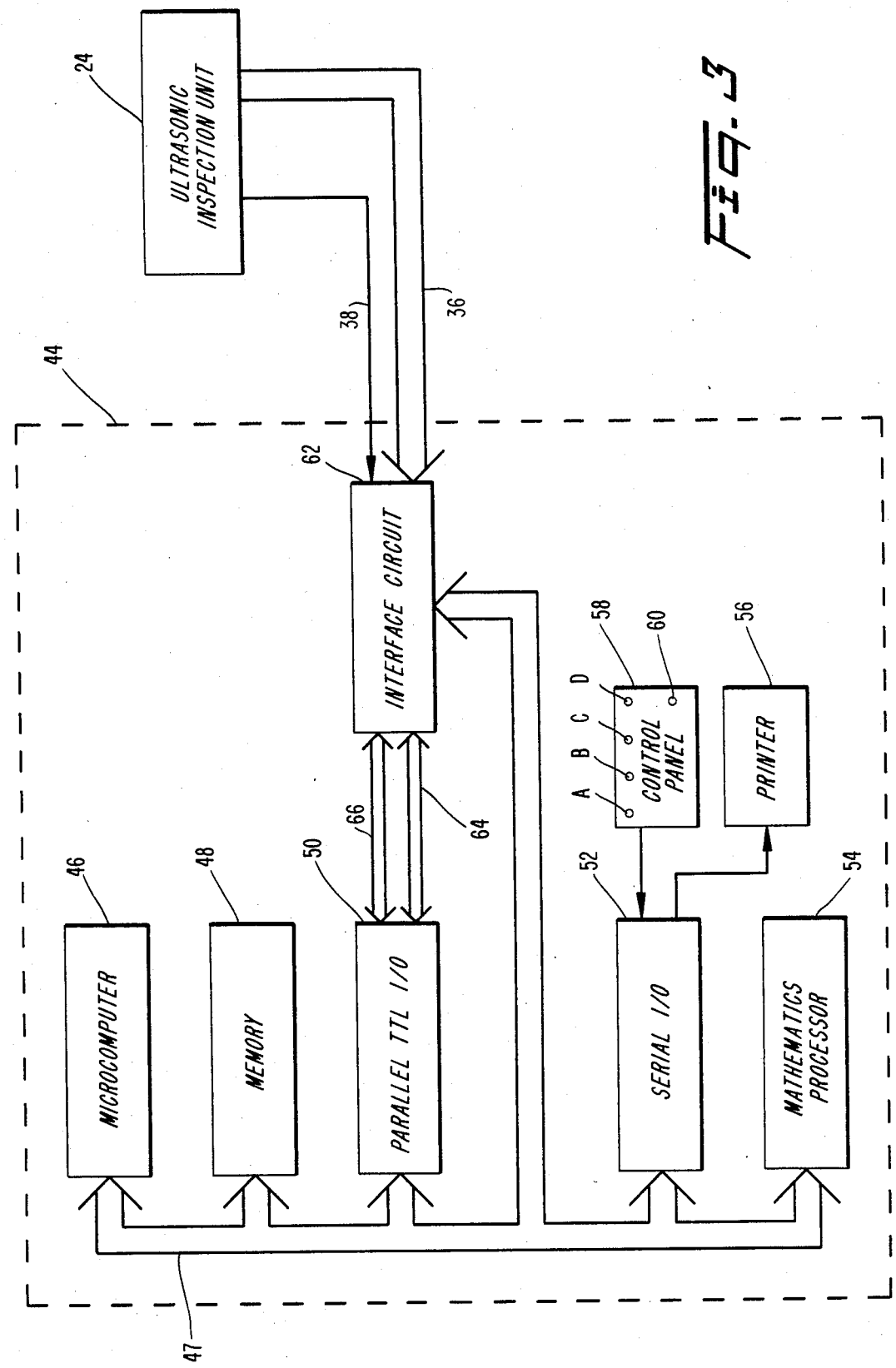

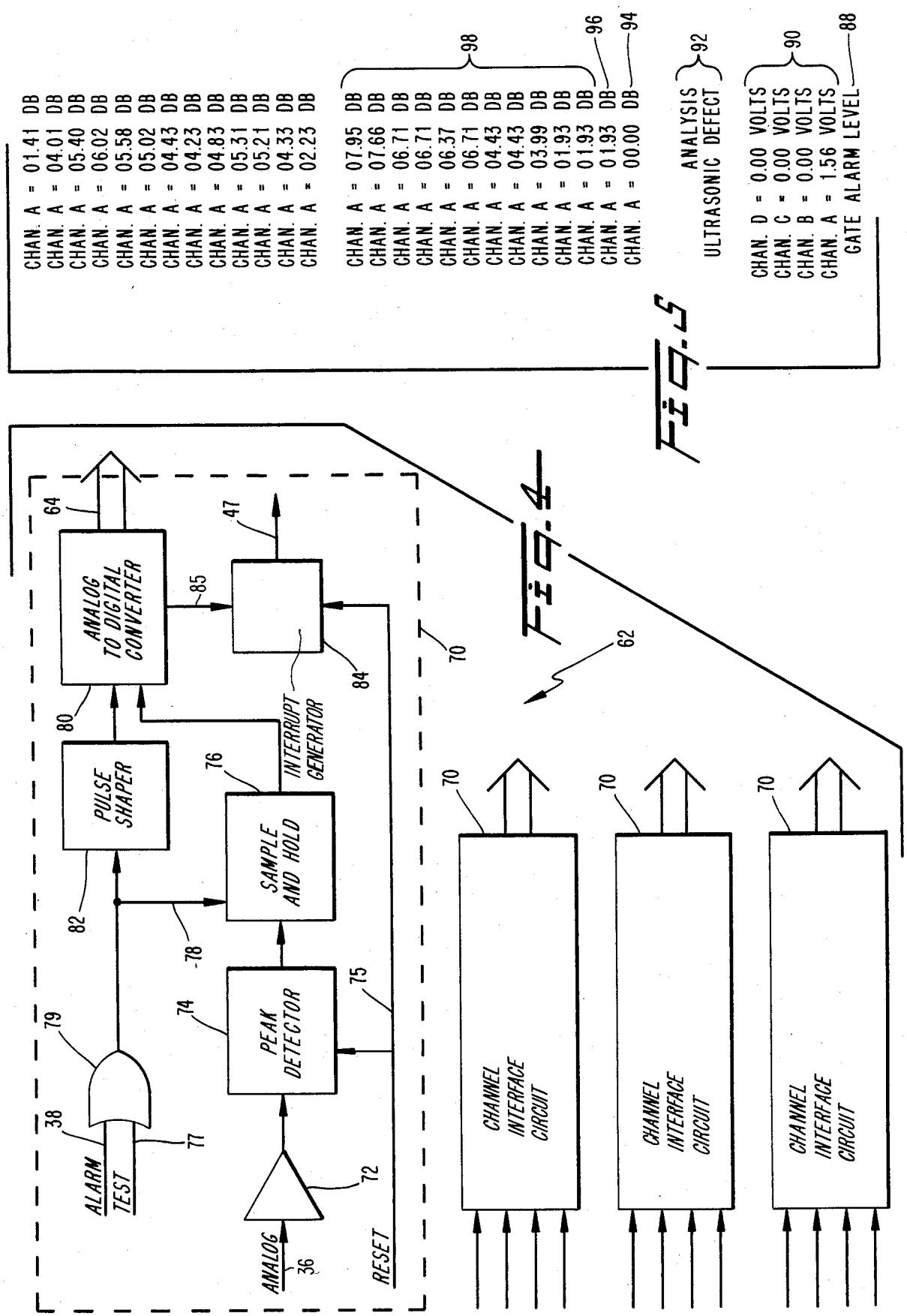

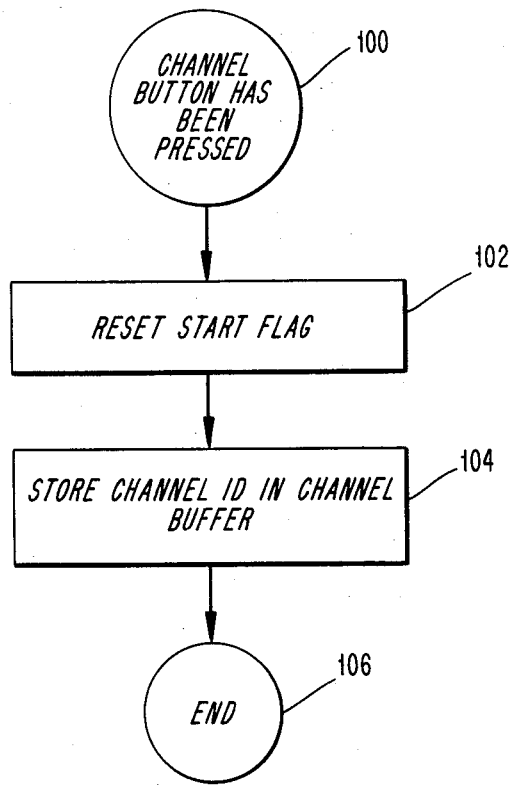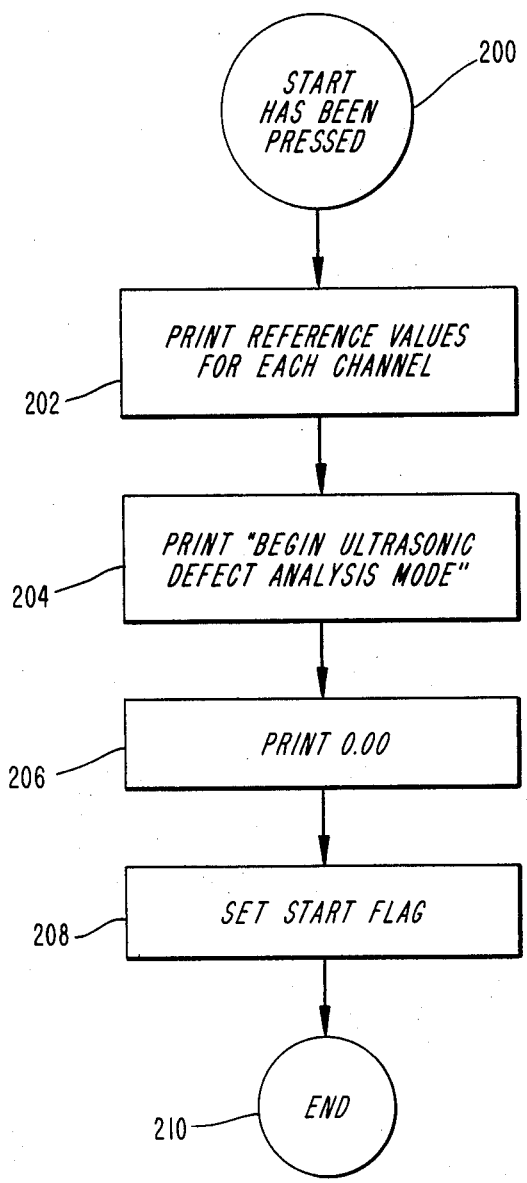

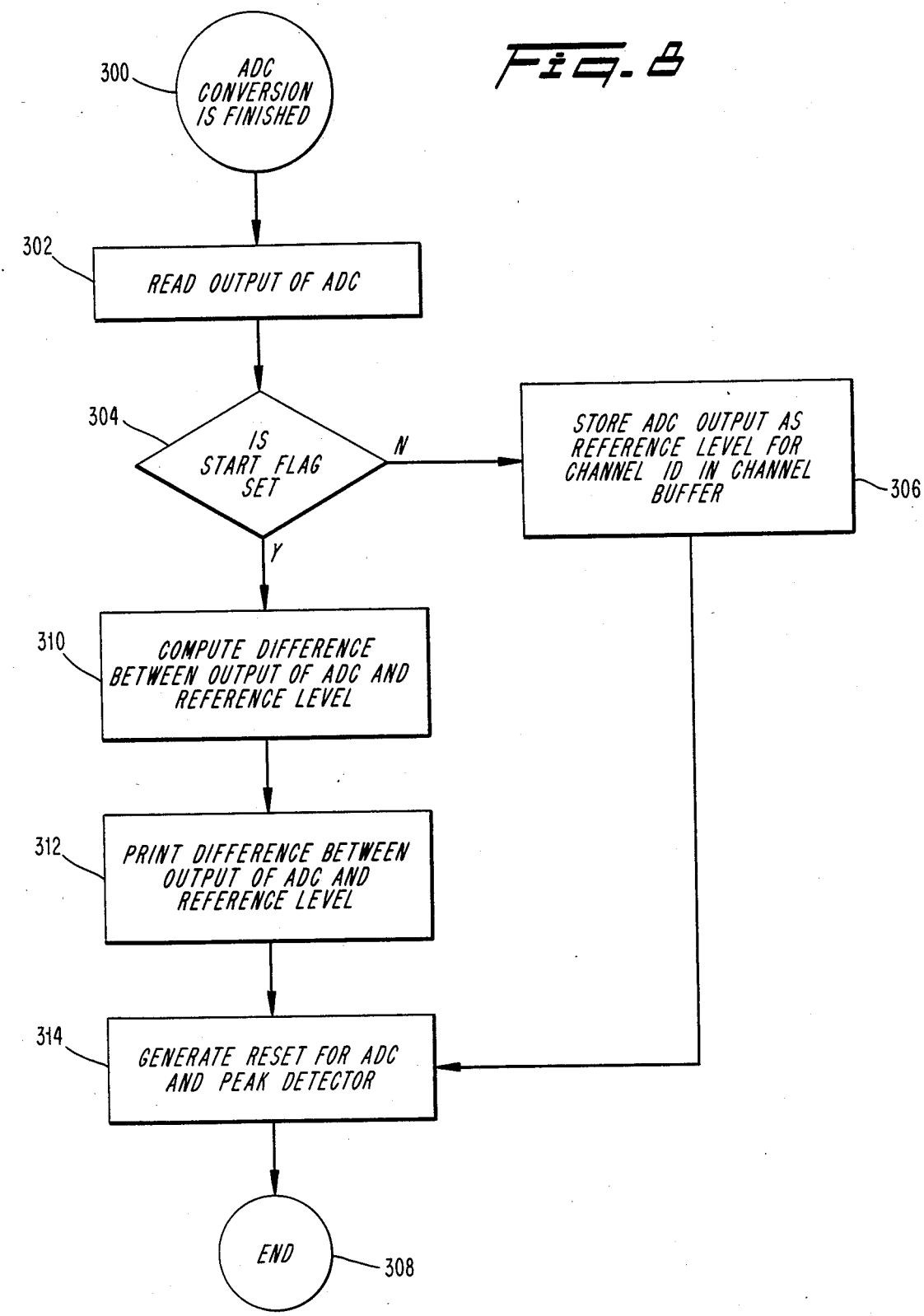

DATA RECORDING APPARATUS FOR AN ULTRASONIC INSPECTION SYSTEM

CROSS REFERENCE TO RELATED APPLICATIONS

The invention is related to the following copending U.S. patent applications assigned to the assignee of the present invention:

ULTRASONIC INSPECTION SYSTEM WITH LINEAR TRANSDUCER ARRAY, Ser. No. 06/815,047, filed on Dec. 31, 1985 by D. P. Sarr and F. D. Young;

ULTRASONIC INSPECTION SYSTEM APPARATUS AND METHOD, Ser. No. 06/815,048, filed on Dec. 31, 1985 by D. P. Sarr;

ULTRASONIC INSTRUMENTATION FOR EXAMINATION OF VARIABLE-THICKNESS OBJECTS, Ser. No. 06/815,038, filed on Dec. 31, 1985 by D. P. Sarr;

AN IMPROVED ULTRASONIC TESTING APPARATUS, Ser. No. 06/815,163, filed Dec. 31, 1985 by G. A. Geithman and D. P. Sarr;

ULTRASONIC TRANSDUCER WITH SHAPED BEAM INTENSITY PROFILE, Ser. No. 06/815,162, filed Dec. 31, 1985 by G.A. Geithman and D. H. Gilbert; and ULTRASONIC 64 CHANNEL INSPECTION SYSTEM WITH MULTIGATE/MULTI MODE SELECTION SOFTWARE CONFIGURABILITY, Ser. No. 06/815,044, filed Dec. 31, 1985 by D. P. Sarr.

The disclosures of these applications are hereby incorporated by reference.

BACKGROUND OF THE INVENTION

The invention relates to data recording apparatus and, more particularly to data recording apparatus suitable for use with ultrasonic testing equipment.

Many types of components for industrial products are inspected using nondestructive testing techniques such as ultrasonic inspection (UI). Various types of UI apparatus are available for providing an indication of defects in components such as seamless tubing.

Pulse-echo ultrasonic inspection equipment generates an ultrasonic signal, detects echo signals, and provides an output signal which is indicative of the presence of a defect in the component being inspected when the echo signal exceeds a reference, or gate, level. Upon indication of such defect, the inspection process is halted and the defective portion of the component is marked. In order to provide more rapid inspection of large components by UI equipment, multiple channels are often employed. If the UI equipment provides an analog output signal indicative of the size of defects, the value of such analog output signal may be manually recorded for each channel.

Although ultrasonic inspection equipment is available which includes the built-in capability for automatic data recording, other types of equipment known as indication-only equipment do not provide for data recording. However, it is often desirable to add automatic data recording capability to existing, lower cost, indication-only apparatus. Moreover, greater flexibility can be obtained if data recording apparatus can be removably connected to indication-only type apparatus to allow a single data recording unit to be selectively connected to a plurality of indication-only ultrasonic inspection units.

Some types of indication-only ultrasonic inspection units provide an output signal calibrated in volts. However, it is difficult to determine the severity of the defect merely from the value of the output signal indication without some indication of the gate level which is being utilized by the ultrasonic inspection equipment to determine it an echo signal represents a defect.

It would therefore be desirable to provide apparatus for recording data from indication-only ultrasonic inspection equipment which can be selectively connected to any of a plurality of indication-only ultrasonic inspection instruments. It is further desirable to provide such capability for a multichannel instrument. It is additionally desirable to provide apparatus for automatically recording ultrasonic inspection defect data and to relate such recorded defect data to the reference level being employed by the UI equipment.

SUMMARY OF THE INVENTION

In accordance with the principles of the present invention, there is provided ultrasonic inspection apparatus comprising an ultrasonic inspection unit generating ultrasonic inspection pulses, supplying the pulses to a part being inspected, producing an output signal proportional to the level of echo pulses received from within a predetermined gate time window following generation of the inspection pulses, and generating an alarm signal whenever the output signal exceeds a predetermined gate level. The apparatus further includes means for storing a value of the output signal as a gate level and means for receiving a plurality of operator-entered signals. The apparatus further comprises means for causing the currently produced value of the output signal to be stored as the gate level upon receipt of a first operator-entered signal. Means are further provided for calculating the difference between the gate level and the output signal upon generation of the alarm signal. Means are also provided for recording the difference as an indication of a defect in a part being inspected.

BRIEF DESCRIPTION OF THE DRAWINGS

FIG. 3 is an electrical block diagram of a preferred embodiment of the present invention;

FIG. 4 is a block diagram of the analog to digital converter circuit shown in FIG. 3;

FIG. 5 is a printout of data recorded by the apparatus of FIG. 1; and

FIGS. 6, 7, and 8 are logic flow diagrams of programs executed by a microcomputer which constitutes a portion of the apparatus of FIG. 1.

DESCRIPTION OF THE PREFERRED EMBODIMENT

Figure 1:
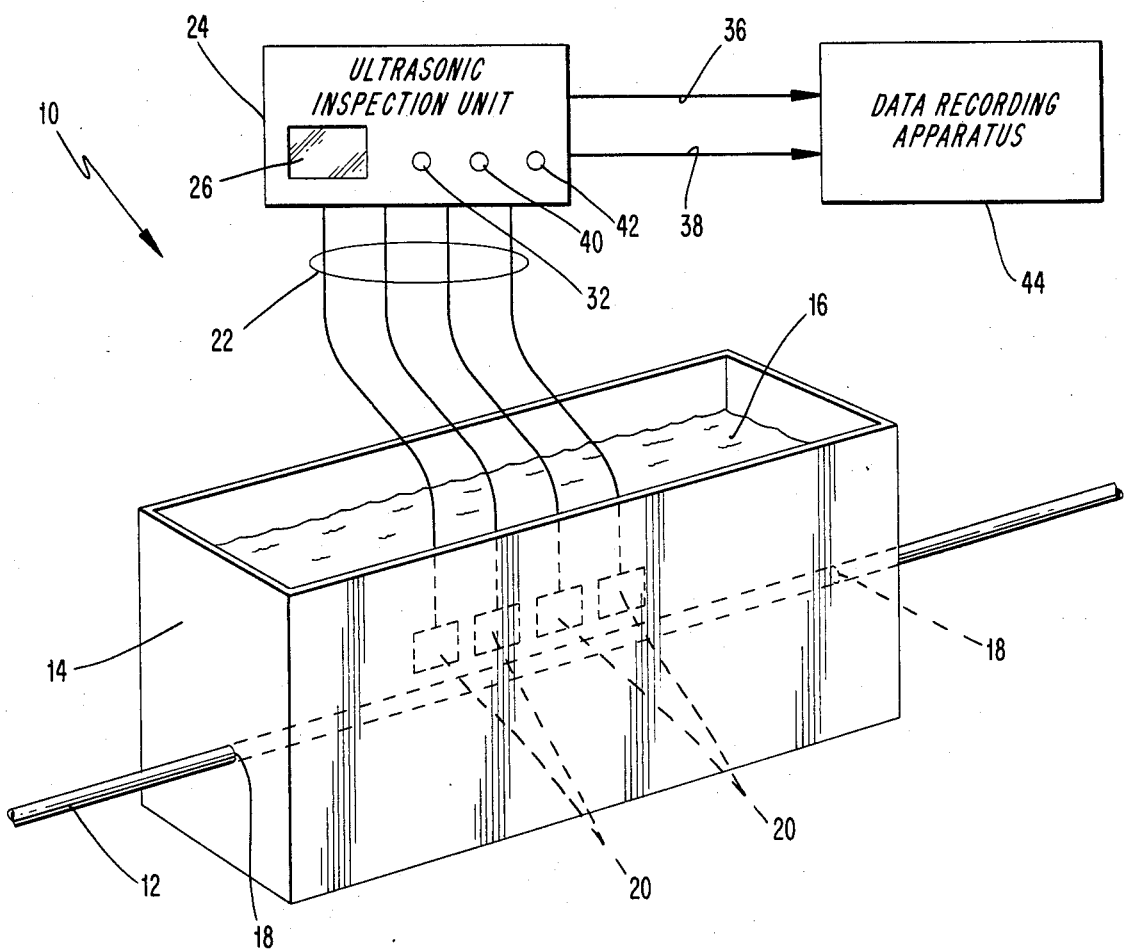
FIG. 1 is a perspective schematic drawing of ultrasonic inspection apparatus which constitutes a preferred embodiment of the present invention.

Referring now to the drawings, in which like reference characters refer to corresponding elements, FIG. 1 shows an ultrasonic inspection and recording system 10 constructed according to the principles of the present invention. The system 10 is designed to provide continuous inspection and recording of data for seamless metal tubing 12. Tubing 12 may be used for purposes such as hydraulic lines in aircraft or coolant lines in electric utility power plants. In the operation of system 10, tubing 12 is fed through a tank 14 filled with water. Apertures 18 are provided in each end of tank 14 and fitted with gaskets or other suitable sealing means, not shown, to permit tubing 12 to be continuously fed through tank 14 from right to left as shown in FIG. 1.

A plurality of ultrasonic transducers 20 are supported by suitable brackets in proximity to tubing 12. Supporting brackets for transducers 20 are well known in the art and are omitted from FIG. 1 for the purposes of clarity. Transducers 20 are connected over electrical cables 22 to an indication-only ultrasonic inspection unit 24. Unit 24, which may be a type S-80 unit commercially available from Automation Industries, Inc., generates electrical pulses at a frequency of approximatly 2-3 Khz to transducers 20, which in turn generate pulses of ultrasonic energy which are supplied to tubing 12. Ultrasonic echo signals are reflected from tubing 12, and are received and converted to electrical signals by transducers 20. The electrical signals are transmitted back to unit 24, which displays the information obtained by the echo pulses on a display panel 26.

Figure 2:
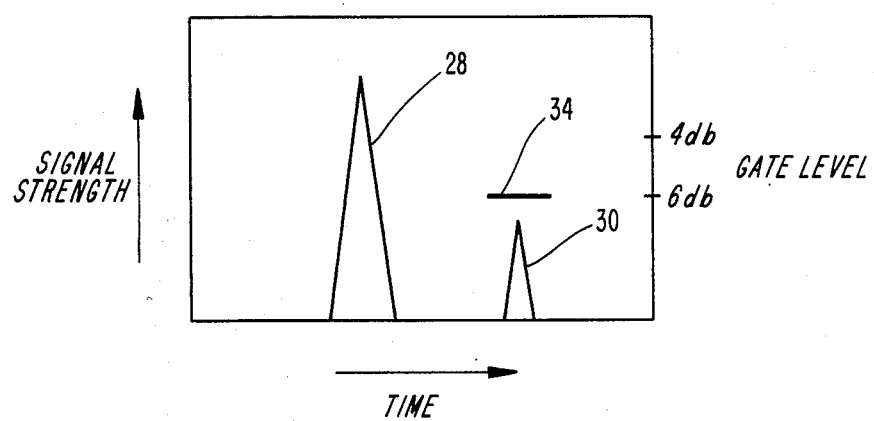
FIG. 2 shows a display provided by indication-only ultrasonic inspection apparatus in the A-scan mode.

The type of information displayed on panel 26 is shown in FIG. 2 and is commonly referred to as an ultrasonic A-scan. In FIG. 2, the vertical axis represents strength of received echo pulses, and the horizontal axis represents time.

It has been determined in certain applications that more meaningful data can be obtained by inspection using a plurality of channels. For example, transducers 20 may be positioned with a slight angular displacement in the circumferential direction with respect to tubing 12. For example, in testing of titanium tubing used for hydraulic lines, four channels have proven especially suitable.

In the preferred embodiment, unit 24 is a four-channel unit, in that provision is made for operation of four separate transducers 20. Panel 26 may be selectively connected to any of the four channels so as to display information received by any or all of transducers 20. Unit 24, according to the present invention, may comprise more or fewer channels. Although four channels are provided in the disclosed embodiment, recording of data from only a single channel will be discussed, for purposes of clarity.

As can be seen in FIG. 2, a strong echo pulse is received from the outer surface of tubing 12. This is indicated at 28 in FIG. 2. A second echo pulse 30 is also shown in FIG. 2, having an amplitude lower than pulse 28 and occurring at a later time. Pulse 30 represents a defect, such as a crack, in tubing 12.

Unit 24 includes a gain control 32 for adjusting the gain of circuitry amplifying echo pulses received from transducers 20 and correspondingly adjusting the height of pulses such as pulses 28 and 30 upon display 26. Unit 24 further includes a gating circuit which provides time and amplitude analysis for received echo pulses. The gating circuit produces an indicator 34 on display 26 as shown in FIG. 2 which provides an indication of the operation of the gating circuit. That is, the height of indicator 34 along the Y axis indicates a gate level, and the position of indicator 34 along the X axis indicates the position of a gate time window relative to the time of generation of ultrasonic test pulses. The length of indicator 34 indicates the length of gate time window during which the gating circuit is active.

The gating circuit is utilized in connection with analog signals 36 and digital alarm signals 38 supplied as outputs by unit 24. That is, analog output signal 36 has a value representative of the level of an echo pulse received during the gate time window established by the gating circuitry and shown by indicator 34. Analog output signals 36 are thus proportional to the height of pulses 30 on display 26. Alarm signal 38 is activated whenever a received echo pulse present within the gate time window of the gating circuit (i.e., an ultrasonic defect response 30) exceeds the gate level represented by the position of indicator 34 on the Y axis of FIG. 2. The position of the gate time window and the gate level are adjustable by means of controls 40 and 42, respectively, in unit 24, as shown in FIG. 1. Unit 24 thus constitutes means for generating ultrasonic inspection pulses, supplying the pulses to a part being inspected, producing an output signal proportional to the level of echo pulses received within a predetermined gate time window following generation of the inspection pulses, and generating an alarm signal whenever the output signal exceeds a predetermined gate level.

During normal operation of unit 24, tubing 12 is simultaneously rotated and moved in an axial direction through tank 14. Unit 24 generates continuous ultrasonic inspection pulses and analyzes received echo pulses from transducers 20. Analog output signals 36, for each channel, constitute continuous analog output signals representative of the strength of received echo pulses present during the gate time window of the gating circuitry of unit 24. Whenever a received echo pulse exceeds the gate level of the gating circuitry as established by control 42, an alarm signal 38 is activated corresponding to the channel in which the excessive echo pulse 30 is received.

Alarm signal 38 may be connected to a suitable alarm indicator such as a buzzer or light. When an operator observes the activation of an alarm signal, appropriate manual actions may be taken, such as marking tubing 12 with a grease pencil where it exits tank 14 and manually recording the level of analog output 36.

In the present invention, however, output signals 36 and 38 of unit 24 are supplied to data recording apparatus 44, the specific construction of which is shown more clearly in FIG. 3. As can be seen therein, recording apparatus 44 includes a microcomputer 46 connected through a multiple-conductor bus 47 to a program memory circuit 48, a parallel, TTL input/output port 50, a serial input/output port 52 configured according to the RS-232C standard, and a mathematics processor chip 54. Microcomputer 46 may be any suitable microcomputer and, in the preferred embodiment, comprises an Intel Model 86-12 microcomputer board. Similarly, memory circuit 48, parallel input/output circuit 50, and serial input/output port 52 may comprise any commercially available circuits of such type suitable for use with the selected microcomputer. In the preferred embodiment, memory circuit 48 constitutes an Intel 464 EPROM memory expansion board, and parallel input/output port 50 and serial input/output port 52 together constitute an Intel 517 serial and parallel expansion board.

Bus 47 may be any suitable multiple-conductor bus, and in the preferred embodiment is configured according to the Intel Multi-Bus protocol.

Mathematics processor 54 comprises a type AM95-11A integrated circuit available from the Advanced Micro Devices Corporation, and suitable interface circuitry well-known to those skilled in the art for connecting the type AM9511A circuit to the Intel Multi-Bus.

Serial input/output port 52 is connected in a well-known manner to a printer 56 which may be any commercially available printer such as a type 202A-002 thermal printer available from the Fluke Corporation.

The invention includes means for receiving a plurality of operator-entered signals. As embodied herein, such receiving means includes a control panel 58 connected to serial input/output port 52 and which constitutes a plurality of momentary contact switches, including channel switches A, B, C, and D and a START switch 60.

Recording apparatus 44 also includes an interface circuit 62 connected by four 8-bit parallel busses 64 and an 8-line bus 66 to parallel input/output port 50. Circuit 62 is also connected to microcomputer 46 via bus 47 and to analog output signals 36 and alarm signals 38 for each channel of unit 24.

The construction of circuit 62 is shown in greater detail in FIG. 4. Circuit 62 includes four identical channel interface circuits 70, one for each channel of unit 24. Each circuit 70 includes an amplifier 72, the input of which is connected to the analog output signal 36 of the corresponding channel of unit 24. The output of amplifier 72 is fed through a peak detector 74 to a sample and hold device 76. Peak detector 74 stores the peak value supplied through amplifier 72 until such time as a reset signal 75 is provided from microcomputer 46 over bus 47. The output of peak detector 74 is continuously supplied to sample and hold device 76 until such time as a command is received over a control line 78 supplied as the output signal from an OR gate 79, the inputs of which are connected to alarm signal 38 for this channel and to a test signal from microcomputer 46. When control line 78 is activated, sample and hold device 76 then latches in the present output of peak detector 74 and supplies such output to an analog-to-digital converter circuit (ADC) 80. The output of OR gate 79 is also supplied through a pulse shaper circuit 82 to ADC 80 for a 5 microsecond conversion.

Reset signal 75 is also, supplied to a interrupt generator circuit 84, the other input line 85 of which is supplied by ADC 80. Circuit 84 is reset by microcomputer 46 initially and after the ultrasonic binary data is read from ADC 80. ADC 80 supplies an end-of-conversion pulse over line 85 to circuit 84 which changes the logic level in the output of circuit 84 which is connected to an interrupt of microcomputer 46 through bus 47.

The operation of system 10 will now be briefly described, followed by a more detailed description in connection with the components of system 10. Prior to actual testing, it is necessary to establish the gate level for each channel which will result in a received echo pulse being considered to represent a defect of tubing 12. After the gate level has been established, normal operation of system 10 begins. The gate level for each channel is then printed on printer 56.

The proper gate level is established for each channel and stored for operation of system 10 in the following manner. A sample section of tubing 12 is positioned in tank 14 in proximity to transducer 20 of the channel for which a gate level is to be established The sample includes a standard defect constituting a notch inscribed on the inner surface of the tubing by an electrical discharge machining operation. Such notch may be provided by manufacturers or fabricators of tubing 12 prior to ultrasonic inspection and is of a precise width and depth.

Unit 24 is then activated to produce periodic ultrasonic testing pulses of standard level. Echo pulses are received by transducer 20 and presented on display 26 as shown in FIG. 2. Pulse 28 represents the reflection from the surface of tubing 12 whereas pulse 30 represents the echo pulse received as a result of the standard defect present in the sample tubing.

The gate time window of unit 24 is adjusted using control 40 so that pulse 30 falls approximately in the center thereof, as shown by indicator 34. Next, the operator presses the channel button A, B, C, or D of control panel 58 associated with the channel for which a gate level is to be established. This provides a signal to microcomputer 46 that the associated channel will be activated and that a gate level is being established for that channel. Next, the gain of unit 24 is increased using control 32, causing the height of pulse 30 to increase. When the height of pulse 30 reaches the gate level as shown by indicator 34, an alarm signal 38 is generated by unit 24 in accordance with the normal conventional operation thereof.

The alarm signal 38 is supplied to interface circuit 62 through OR gate 79 of circuit 70, resulting in activation of sample and hold circuit 76 and ADC circuit 80. Thus, the analog signal produced by unit 24 in response to an echo pulse caused by the standard defect in sample tubing 12 is converted to a digital quantity and supplied over bus 64 through parallel input/output circuit 50 to microcomputer 46. Microcomputer 46 then stores the received digital value in its internal memory as the gate level for the corresponding channel of unit 24.

An alternative method of establishing a gate level for the channel may be employed. As in the previously described method, a standard defect in sample tubing 12 is placed in proximity to transducer 20 of the channel for which a reference level is to be established. The gate level of unit 24 for the selected channel is adjusted by control 42 to a high level. The associated channel button A, B, C, or D of control panel 58 is then pressed by the operator This informs microcomputer 46 the channel for which a gate level is being established. Again, pulse 30 shown in FIG. 2 is produced on display 26 of unit 24 by echo pulses from the standard defect. Unlike the previously described method, the gain of the unit 24 is not adjusted in establishing the gate level. Rather, the gate level control 42 is adjusted to gradually lower the gate level in the direction of the top of pulse 30.

The gate level is continued to be reduced, until such time as the gate level is equal to the peak of pulse 30 present within the gate time window. At such time, alarm signal 38 is activated. Alarm signal 38 then causes the present value of analog output signal 36 (i.e., the level of pulse 30 caused by the standard defect) to be latched by sample and hold circuit 76 and converted by ADC circuit 80 into a digital quantity for transmission to microcomputer 46. The received digital quantity is then stored in the internal memory of microcomputer 46 as the gate level for the associated channel.

The invention thus includes means for storing a value of output signal 36 as a reference level and means for causing the currently produced value of the output signal to be stored as a reference level upon receipt of a first operator-entered signal and an alarm signal. As can be seen in FIG. 3, microcomputer 46, circuit 62, and parallel input/output port 50 store a value of output signal 36 when an activation of a channel button A, B, C, or D is followed by generation of an alarm signal.

If additional channels are to be activated, gate levels are established for such channels in a similar manner, by pressing the appropriate channel button A, B, C, or D and adjusting the gain or gate level of unit 24.

After gate levels for all channels have been established, normal operation of system 10 is begun, including automatic recording of defect data on printer 56. A sample printout of such automatic data recordation is shown in FIG. 5. In the specific disclosed embodiment, the printout provided by printer 56 shown in FIG. 5 reads from bottom to top.

Normal operation is initiated when an operator activates START push button 60 of control panel 58 to place system 10 in the defect analysis mode. Program instructions stored in memory 48 cause microcomputer 46 to first print out a message 88 of FIG. 5 on printer 56, followed by the gate levels, in volts, for each channel which has been activated prior to activation of START push button 60. If one or more channels do not have gate levels entered therefore, such channels will not be activated. Inactive channels are indicated by a printout of 0.00 volts, as can be seen in FIG. 5 at 90. Next, a message 92 is printed, indicating that normal inspection and data recording of system 10 has begun. After activation of START button 60, microcomputer 46 causes printer 56 to print a data point of 00.00 dB, as shown in FIG. 5 as item 94.

Tubing 12 is then fed through tank 14 in the normal manner, and unit 24 generates ultrasonic inspection pulses over each active channel. An echo pulse received during the gate time window established by adjustment of control 40 of unit 24 is presented on display 26 in the normal manner. However, no data is produced by printer 56 so long as the level of a received echo pulse is below the previously established gate level stored as a reference level for that channel. If a defect occurs in tubing 12 as it is fed through tank 14 past transducers 20, an echo pulse is received within the gate time window for the appropriate channel which has level greater than the previously established gate level. Alarm signal 38 for the associated channel is then activated. Alarm signal 38 causes sample and hold circuit 76 of the associated channel conversion circuit 70 to latch the current value of peak detector 74, which represents the value of the echo pulse produced by the detected defect. This analog signal is converted to a digital value by ADC circuit 80 and supplied to microcomputer 46.

The digital value of the analog signal produced by the detected defect is converted to a decibel level referenced to the stored gate level for the associated channel. This conversion is provided by mathematics processor circuit 54 under control of microcomputer 46 according to the following formula:

$$db = 20 \log \left( \frac{V_{pk} \text{ of UI Signal}}{V_{gate \text{ reference}}} \right)$$

where $V_{pk}$ is the value of the analog signal and $V_{gate}$ reference is the stored reference level. Mathematics processor circuit 54 provides extremely rapid calculation of the decibel value which is important for many applications. In other applications, such high speed may not be necessary and the decibel value or other appropriate calculations can be provided directly by microcomputer 46.

The decibel value produced by mathematics processor circuit 54 is then transmitted by microcomputer 46 through serial input/output circuit 52 to printer 56. The decibel value is then printed by printer 56 along with an indication of the associated channel, as shown at 96 in FIG. 5.

The invention thus includes means for calculating the relationship between the reference level and output signal 36 upon receipt of a second operator-entered signal followed by an alarm signal, and means for recording the relationship as an indication of a defect in a part being inspected. As can be seen in FIGS. 3 and 5, microcomputer 46 and mathematics processor circuit 54 calculate the decibel relationship between the reference level and the value of output signal 36 upon activation of START switch 60 followed by generation of alarm signal 38. Microcomputer 46, through serial input/output port 52, then causes printer 56 to print the decibel relationship.

In a similar manner, each time a defect in tubing 12 causes generation of an echo pulse 30 above the stored gate level, a decibel value representative of the echo pulse from the detected defect will be printed by printer 56. As tubing 12 is rotated and advanced through tank 14, a defect will initially be detected as a fairly low-level echo pulse and will increase, as the center of the defect is rotated directly below the associated tranducer 20. Echo pulses produced by such defect will accordingly increase in level until such time as the defect is directly below the associated transducer 20. Such effect can be clearly seen at 98 in FIG. 5, as the decibel values associated with a defect present in a rotating tube cause decibel values to be printed, ranging from 1.93 dB as the defect is first brought within range of transducer 20 through a value of 7.95 dB as the defect is directly beneath transducer 20.

The present invention allows data recording capability to be applied to an existing indication-only ultrasonic inspection unit without modification of the exiting unit. Moreover, such capability may be provided with a plurality of ultrasonic inspection units without modification of either the ultrasonic inspection unit 24 or the data recording system 44.

The operation of microcomputer 46 is controlled by program instructions stored in memory 48. FIG. 6 shows the logic flow of the program instructions for establishment of the gate level. An interrupt is enabled upon activation of a channel button A, B, C, or D, causing an interrupt handler routine to activate the program shown in FIG. 6. Block 100 indicates the start of such program. In block 102 a START flag, used with a routine to be executed later, is reset. The identity of the channel button just activated is stored in a channel buffer at block 104. The gate level setting routine ends at block 106.

Microcomputer 46 provides normal data recording operation of system 10 following activation of START push button 60 as shown in FIG. 7. Activation of START push button 60 generates a signal to microcomputer 46 which causes execution of the logic flow beginning at block 200. The reference values for each activated channel are printed out at block 202. An indicator message is printed at block 204. Next at block 206, the value of 0.00 decibels is printed as the first data point to indicate that reference values for all active channels have been stored and that the system is now entering the ultrasonic defect analysis mode. The START flag is then set at block 208 and the routine ends at block When the alarm signal 38 for a channel is activated, the current value of the analog output signal 36 for that channel is latched by sample and hold circuit 76 of the associated channel circuit 70, and an analog-to-digital conversion of that value provided by ADC circuit 80. Upon completion of the conversion, an interrupt is generated by circuit 84 in response to a signal from ADC circuit 80, causing microcomputer 46 to access the routine shown in FIG. 8. This routine begins at block 300 and causes the output of the ADC circuit 80 which generated the interrupt to be read at block 302. Next a determination is made at block 304 if the START flag is set. If not, this is an indication that the alarm signal has been generated in connection with the process of establishing the gate level. Accordingly, the digital value read at block 302 is stored as the gate level for the channel indicated by the contents of channel buffer, previously stored in the routine of FIG. 6. A reset signal is generated to reset ADC 80 and peak detector 74, and the routine of FIG. 8 ends at block 308.

If it is determined at block 304 that the START flag has been set, this is an indication that the alarm signal was generated in connection with an actual defect detected during the ultrasonic defect analysis mode. Accordingly, microcomputer 46 at block 310 activates mathematics processor circuit 54 to compute the difference between the ADC output value read at block 302 and the reference value for the associated channel. This difference value is then printed on printer 56 at block 312. A reset signal 75 is then generated at block 314 to reset peak detector 74 and circuit 84. The routine ends at block 308, and awaits the generation of the next alarm signal.

It will be apparent to those skilled in the art that various modifications and variations can be made in the present invention without departing from the scope and spirit of the invention. For example, other types of calculations could easily be provided by microcomputer 46 or mathematics processor circuit 56. Thus, it is intended that the present invention cover the modifications and variations of this invention provided they come within the scope of the appended claims and their equivalents.

What is claimed is:

1. Ultrasonic inspection apparatus, comprising:
    ultrasonic inspection means for generating ultrasonic inspection pulses, for supplying said pulses to a part being inspected, for producing an output signal proportional to the level of echo pulses received within a predetermined gate time window following generation of said inspection pulses, and for generating an alarm signal whenever said output signal exceeds a predetermined gate level;
    means for storing a value of said output signal as a reference level;
    means for receiving a plurality of operator-entered signals;
    means for causing the currently produced value of said output signal to be stored as said reference level upon receipt of a first operator-entered signal and said alarm signal;
    means for calculating the relationship between said reference level and said output signal upon receipt of a second operator-entered signal and said alarm signal; and
    means for recording said relationship as an indication of a defect in a part being inspected.

2. Apparatus for recording ultrasonic inspection data generated by an ultrasonic inspection unit generating ultrasonic inspection pulses, supplying said pulses to a part being inspected, producing an output signal proportional to the level of echo pulses received from within a predetermined gate time window following generation of said inspection pulses, and generating an alarm signal whenever said output signal exceeds a predetermined gate level, said apparatus comprising:
    means for storing a value of said output signal as a reference level;
    means for receiving a plurality of operator-entered signals;
    means for causing the currently produced value of said output signal to be stored as said reference level upon receipt of a first operator-entered signal and said alarm signal;
    means for calculating a relationship between said reference level and said output signal upon receipt of a second operator-entered signal and said alarm signal; and
    means for recording said relationship as an indication of a defect in a part being inspected.

3. Apparatus for recording ultrasonic inspection data generated by an ultrasonic inspection unit generating ultrasonic inspection pulses, supplying said pulses to a part being inspected, producing an output signal proportional to the level of echo pulses received from within a predetermined gate time window following generation of said inspection pulses, and generating an alarm signal whenever said output signal exceeds a predetermined gate level, said apparatus comprising:
    an interface circuit connected to said inspection unit and generating a digital signal corresponding to said output signal upon receipt of an alarm signal;
    input means for receiving a plurality of operator-entered input signals;
    a data recorder; and
    control means connected to said input means and to said interface circuit, said control means being responsive to a first operator-entered input signal for storing a value of said digital signal as a reference signal, and responsive to a second operator-entered input signal for computing the difference between subsequent values of said digital signal and said reference signal, and for causing said data recorder to record a value indicative of said difference.

4. Apparatus as recited in claim 3 wherein said interface circuit comprises:
    a peak detector connected to said inspection unit for generating a detector output signal corresponding to the peak value of said inspection unit output signal;
    an analog-to-digital converter coupled to said peak detector and producing a digital value corresponding to said detector output signal; and
    an activating circuit for commanding said analog-to-digital converter to produce a first digital signal corresponding to the output of said peak detector upon detection of an alarm signal.

5. Apparatus as recited in claim 4 wherein said control means comprises a microcomputer and a mathematics processor circuit.

6. A method for recording ultrasonic inspection data generated by ultrasonic inspection apparatus which provides an output signal proportional to the strength of ultrasonic signals received within a gate window from a part being inspected and which generates an alarm signal when the output signal reaches a gate level, said method comprising the steps of:

generating first values of said output signal from said apparatus from a part having a known configuration;

adjusting said ultrasonic inspection apparatus until one of said first values exceeds said gate level to cause said alarm signal to be generated;

storing the level of said one of said first values as a reference level;

operating said apparatus upon a part to be inspected; and recording, upon receipt of said alarm signal, a signal indicative of a defect in the part being inspected.

7. A method as recited in claim 6, comprising the additional step of recording the reference level prior to operating the apparatus.

8. A method as recited in claim 7 wherein the reference level is recorded as a voltage level and the difference is recorded in decibels.

9. A method as recited in claim 6, wherein the step of recording a signal indicative of a defect comprises the steps of calculating the difference between the stored reference level and the level of a second output signal generated concurrently with the alarm signal, and recording the difference.

10. A method as recited in claim 6 wherein said step of adjusting said ultrasonic inspection apparatus comprises the step of adjusting the gain of the ultrasonic inspection apparatus until an alarm signal is generated.

11. A method as recited in claim 6 wherein the step of adjusting said ultrasonic inspection apparatus comprises the step of adjusting the gate level until an alarm signal is generated.

* * * * *